United States Patent
Lee

(10) Patent No.: US 9,763,776 B2
(45) Date of Patent: Sep. 19, 2017

(54) ASYMMETRIC CAPSULAR RING FOR INHIBITING CAPSULAR OPACIFICATION

(71) Applicant: NOVARTIS AG, Basel (CH)

(72) Inventor: Sung Kyu Lee, Euless, TX (US)

(73) Assignee: Novartis AG, Basel (CH)

( * ) Notice: Subject to any disclaimer, the term of this patent is extended or adjusted under 35 U.S.C. 154(b) by 41 days.

(21) Appl. No.: 14/834,130

(22) Filed: Aug. 24, 2015

(65) Prior Publication Data
US 2016/0220355 A1 Aug. 4, 2016

Related U.S. Application Data

(60) Provisional application No. 62/111,723, filed on Feb. 4, 2015.

(51) Int. Cl.
*A61F 2/16* (2006.01)

(52) U.S. Cl.
CPC .... *A61F 2/1694* (2013.01); *A61F 2230/0065* (2013.01); *A61F 2230/0069* (2013.01); *A61F 2250/0014* (2013.01)

(58) Field of Classification Search
CPC ........ A61F 2/1648; A61F 2/16; A61F 2/1613; A61F 2/1629; A61F 2/1602; A61F 2/14; A61F 2/147; A61F 2/1635; A61F 2/1694; A61F 9/0017; A61F 9/00781
See application file for complete search history.

(56) References Cited

U.S. PATENT DOCUMENTS

| | | | |
|---|---|---|---|
| 5,275,624 A | 1/1994 | Hara et al. | |
| 9,095,424 B2 | 8/2015 | Kahook et al. | |
| 9,125,736 B2 | 9/2015 | Kahook et al. | |
| 9,289,287 B2 | 3/2016 | Kahook et al. | |
| 9,364,316 B1 | 6/2016 | Kahook et al. | |
| 9,387,069 B2 | 7/2016 | Kahook et al. | |
| 9,421,088 B1 | 8/2016 | Kahook et al. | |
| 2008/0275461 A1 | 11/2008 | Nallakrishnan | |
| 2014/0172089 A1 | 6/2014 | Lee et al. | |
| 2015/0230981 A1 | 8/2015 | Kahook et al. | |
| 2015/0289970 A1 | 10/2015 | Akura | |
| 2016/0235587 A1 | 8/2016 | Kahook et al. | |
| 2016/0278912 A1 | 9/2016 | Kahook et al. | |

FOREIGN PATENT DOCUMENTS

WO 2014029383 A2 2/2014
WO 2014103564 A1 7/2014

OTHER PUBLICATIONS

Hara, et al., "Long-term Study of Posterior Capsular Opacification Prevention With Endocapsular Equator Rings in Humans", Arch Ophthalmol, 129:7, Jul. 2011, pp. 855-863.
PCT/US2015/046580; International Search Report, International Searching Authority, Nov. 24, 2015, 2 pgs.

*Primary Examiner* — David H Willse
*Assistant Examiner* — Tiffany Shipmon

(57) ABSTRACT

A capsular ring for insertion into a capsular bag of a patient's eye includes an anterior ring defining a first opening and having a first cross-sectional width and a posterior ring defining a second opening and having a second cross-sectional width. A diameter of the first opening is greater than a diameter of the second opening, and the second cross-sectional width is greater that the first cross-sectional width. The capsular ring further includes a sidewall connecting the first ring and the second ring, the sidewall comprising a plurality of orifices spaced circumferentially around the sidewall.

9 Claims, 6 Drawing Sheets

ASYMMETRIC CAPSULAR RING FOR INHIBITING CAPSULAR OPACIFICATION

This application claims the priority of U.S. Provisional Application No. 62/111,723 filed Feb. 4, 2015 which is hereby incorporated herein by reference in its entirety.

FIELD

This present disclosure relates generally to cataract surgery and, more particularly, to an asymmetric capsular ring for inhibiting capsular opacification.

BACKGROUND

Visually impairing cataract, or clouding of the lens, is the leading cause of preventable blindness in the world. Presently, cataracts are treated by surgical removal of the affected lens and replacement with an artificial intraocular lens ("IOL"). FIG. 1 is a diagram of an eye 100 illustrating anatomical structures related to the surgical removal of a cataract and the implantation of an IOL. The eye 100 comprises an opacified lens 102, an optically clear cornea 104, and an iris 106. A lens capsule (capsular bag 108) located behind the iris 106 of the eye 100 contains the opacified lens 102. More particularly, the opacified lens 102 is seated between an anterior capsule segment (anterior capsule 110) and a posterior capsular segment (posterior capsule 112). The anterior capsule 110 and the posterior capsule 112 meet at an equatorial region 114 of the capsular bag 108. The eye 100 also comprises an anterior chamber 116 located in front of the iris 106 and a posterior chamber 118 located between the iris 106 and the capsular bag 108.

A common technique for cataract surgery is extracapsular cataract extraction ("ECCE"), which involves the creation of an incision near the outer edge of the cornea 104 and an opening in the anterior capsule 110 (i.e., an anterior capsulotomy) through which the opacified lens 102 is removed. The lens 102 can be removed by various known methods. One such method is phacoemulsification, in which ultrasonic energy is applied to the lens to break it into small pieces that are aspirated from the capsular bag 108. Thus, with the exception of the portion of the anterior capsule 110 that is removed in order to gain access to the lens 102, the capsular bag 108 may remain substantially intact throughout an ECCE. The intact posterior capsule 112 provides a support for the IOL and acts as a barrier to the vitreous humor within the posterior chamber 120 of the eye 100. Following removal of the opacified lens 102, an artificial IOL, which may be designed to mimic the transparency and refractive function of a healthy lens, is typically implanted within the capsular bag 108 through the opening in the anterior capsule 110. The IOL may be acted on by the zonular forces exerted by a ciliary body 122 and attached zonules 124 surrounding the periphery of the capsular bag 108. The ciliary body 122 and the zonules 124 anchor the capsular bag 108 in place and facilitate accommodation, the process by which the eye 100 changes optical power to maintain a clear focus on an image as its distance varies.

A frequent complication of ECCE and other forms of cataract surgery is opacification of the posterior capsule 112. Posterior capsule opacification ("PCO") results from the migration of residual lens epithelial cells from the equatorial region 114 of the capsular bag 108 toward the center of the posterior capsule 112. One factor contributing to the development of PCO is contact between the IOL and the surface of the posterior capsule 112. Subsequent to ECCE, the lens epithelial cells may proliferate between the IOL and the surface of the posterior capsule 112, leading to wrinkling and clouding of the normally clear posterior capsule 112. If clouding of the posterior lens capsule 112 occurs within the visual axis, then the patient will experience a decrease in visual acuity and may require additional surgery to correct the patient's vision.

A widely utilized procedure to clear the visual axis of PCO is Neodymium: Yttrium-Aluminum-Garnet ("Nd/YAG") laser capsulotomy, in which a laser beam is used to create an opening in the center of the cloudy posterior capsule 112. However, Nd/YAG laser capsulotomy exposes patients to the risk of severe complications that can lead to significant visual impairment or loss, such as retinal detachment, papillary block glaucoma, iris hemorrhage, uveitis/vitritis, and cystoid macula edema. Moreover, the laser energy is ordinarily directed though the IOL, which may damage the optics of the implant or disrupt its placement within the capsular bag 108. Accordingly, there exists a need to prevent the occurrence of PCO rather than treating PCO at a later date after implantation of an IOL.

SUMMARY

The present disclosure concerns an asymmetric capsular ring designed to inhibit PCO and facilitate safe insertion of a lens once implanted in the capsular bag of a patient's eye. In certain embodiments, a capsular ring for insertion into a capsular bag of a patient's eye includes an anterior ring defining a first opening and having a first cross-sectional width and a posterior ring defining a second opening and having a second cross-sectional width. A diameter of the first opening is greater than a diameter of the second opening, and the second cross-sectional width is greater that the first cross-sectional width. The capsular ring further includes a sidewall connecting the first ring and the second ring, the sidewall comprising a plurality of orifices spaced circumferentially around the sidewall.

Once inserted into the capsular bag of a patient's eye, the above-described capsular ring may inhibit PCO by (1) keeping the capsular bag open to facilitate circulation of aqueous humor into the capsular bag, and (2) engaging the equatorial region of the capsular bag in a manner that inhibits migrations of lens epithelial cells from the equatorial region. In addition, the asymmetric design of the capsular ring (i.e., the posterior ring being greater in width than the anterior ring) may facilitate safe insertion of a lens by helping to guide one or more haptics of the lens into a proper plane (between the posterior and anterior rings) rather than an area of the capsular bag posterior to the capsular ring.

BRIEF DESCRIPTION OF THE DRAWINGS

For a more complete understanding of the present disclosure and the advantages thereof, reference is now made to the following description taken in conjunction with the accompanying drawings in which like reference numerals indicate like features and wherein.

Figure 1:
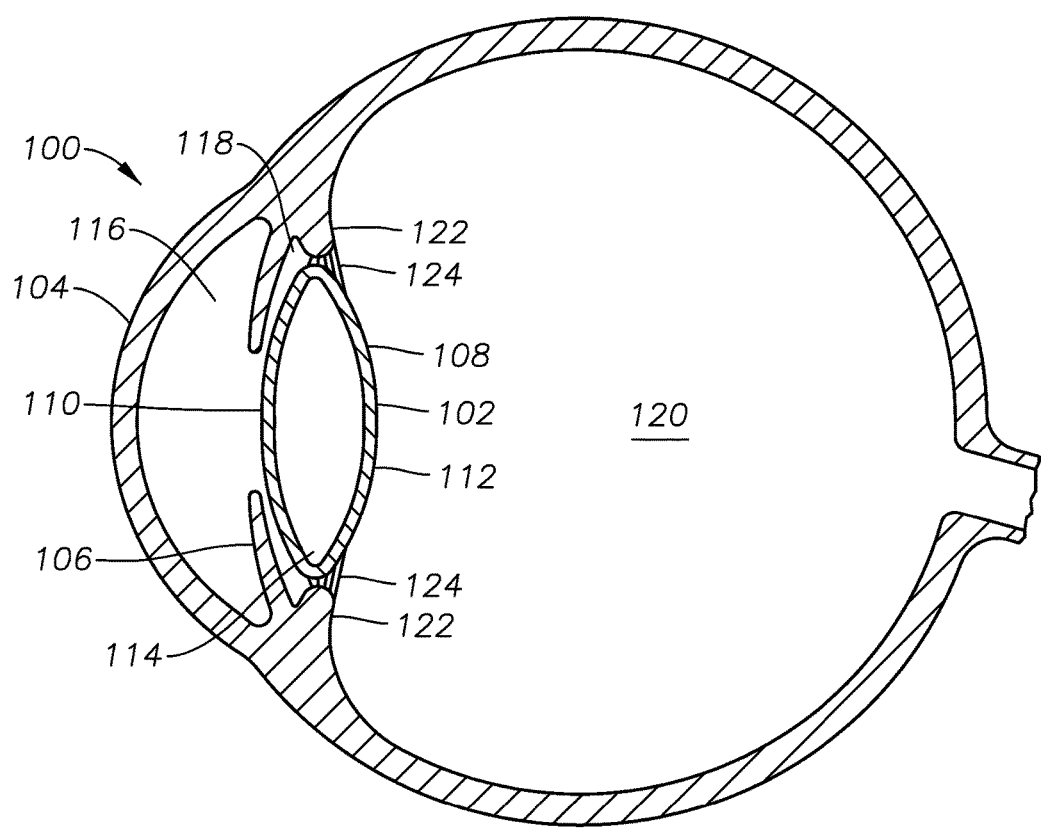
FIG. 1 is a diagram of an eye illustrating anatomical structures related to the surgical removal of a cataract and the implantation of an IOL.

The skilled person in the art will understand that the drawings, described below, are for illustration purposes only. The drawings are not intended to limit the scope of the applicant's disclosure in any way.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described systems, devices, and methods, and any further application of the principles of the present disclosure are fully contemplated as would normally occur to one skilled in the art to which the disclosure relates. In particular, it is fully contemplated that the systems, devices, and/or methods described with respect to one embodiment may be combined with the features, components, and/or steps described with respect to other embodiments of the present disclosure. For the sake of brevity, however, the numerous iterations of these combinations will not be described separately. For simplicity, in some instances the same reference numbers are used throughout the drawings to refer to the same or like parts.

In general, the present disclosure relates to an asymmetric capsular ring designed to inhibit PCO and facilitate safe insertion of a lens once implanted in the capsular bag of a patient's eye. In some instances, embodiments of the present disclosure comprise a capsular ring constructed of an anterior ring and a posterior ring connected by a sidewall, the posterior ring being greater in width than the anterior ring. Once inserted into the capsular bag of a patient's eye, the capsular ring may inhibit PCO by (1) keeping the capsular bag open to facilitate circulation of aqueous humor into the capsular bag, and (2) engaging the equatorial region of the capsular bag in a manner that inhibits migrations of lens epithelial cells from the equatorial region. In addition, the asymmetric design of the capsular ring (i.e., the posterior ring being greater in width than the anterior ring) may facilitate safe insertion of a lens by helping to guide one or more haptics of the lens into a proper plane (between the posterior and anterior rings) rather than an area of the capsular bag posterior to the capsular ring.

Figure 2A:
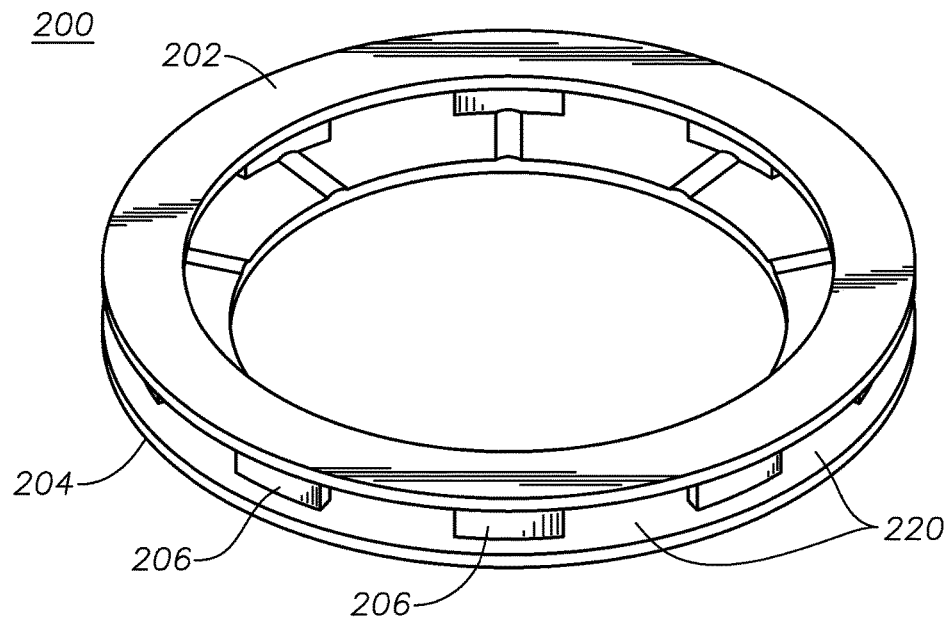
FIGS. 2A-2B illustrate an exemplary asymmetric capsular ring, according to certain embodiments of the present disclosure.
Figure 2B:
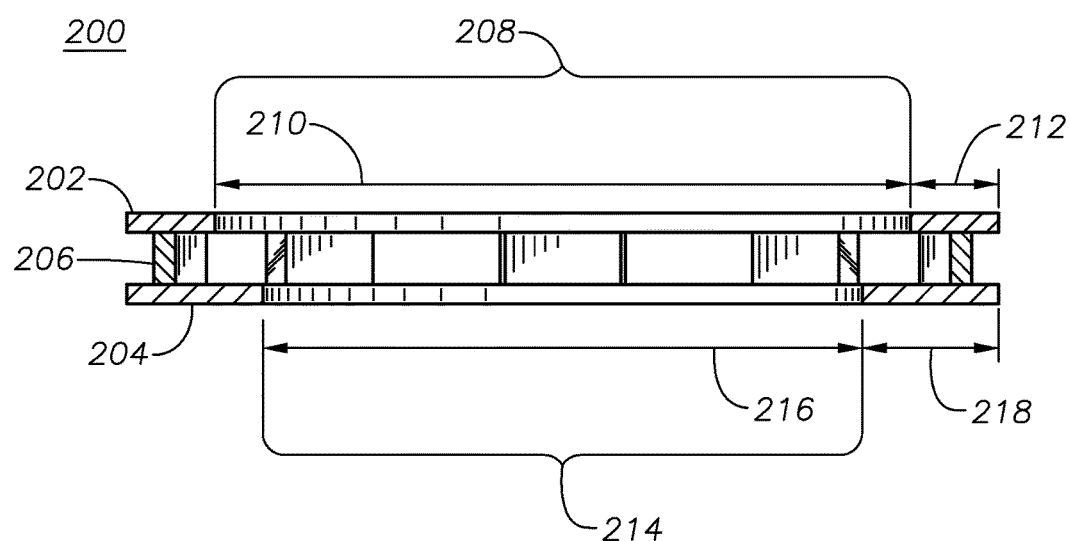

FIGS. 2A-2B illustrate an exemplary asymmetric capsular ring 200, according to certain embodiments of the present disclosure. Capsular ring 200 may include an anterior ring 202 and a posterior ring 204, and the anterior ring 202 may be coupled to the posterior ring 204 via a sidewall 206. As used herein, the terms "anterior" and "posterior" refer to relative positions along the visual axis when implanted in the capsular bag of an eye 100.

Anterior ring 202, when in the depicted expanded (i.e., unstressed) position, may define a generally circular central opening 208 having a diameter 210. Additionally, anterior ring 202 may have a generally rectangular cross section having a width 212. Similarly, posterior ring 204, when in the depicted expanded (i.e., unstressed) position, may define a generally circular central opening 214 having a diameter 216 and may have a generally rectangular cross section having a width 218.

In certain embodiments, the width 218 of posterior ring 204 may be greater than the width 212 of anterior ring 202. Moreover, anterior ring 202 and posterior ring 204 may have substantially the same outer diameter and may be coupled to one another (via sidewall 206, discussed below) such that the outer edges anterior ring 202 and posterior ring 204 generally align (as depicted in FIG. 2B). As a result, diameter 210 of opening 208 defined by anterior ring 202 may be greater than the diameter 216 of opening 214 defined by posterior ring 204.

Although anterior ring 202 and posterior ring 204 are each depicted and described as having a rectangular cross section, the present disclosure contemplates that anterior ring 202 and posterior ring 204 may each have any suitable cross-sectional shape with the width 218 of posterior ring 204 being greater than the width 212 of anterior ring 202. For example, in certain embodiments, posterior ring 204 may comprise a rectangular cross section that additionally includes one or more raised portions (e.g., bumps) on its anterior surface. These raised portions may help reduce friction between the anterior surface of posterior ring 204 and a lens engaged with capsular ring 200 (as discussed with regard to FIG. 6, below).

Sidewall 206 may couple anterior ring 202 to posterior ring 206 in the above-described configuration. In certain embodiments, sidewall 206 may have an outer diameter less than the outer diameter of anterior ring 202 and posterior ring 206 such that, when implanted in the capsular bag 108 of a patient's eye 100, an equatorial void is created in the equatorial region 114 of the capsular bag 108 (as described in further detail below). Additionally, sidewall 206 may include a plurality of orifices 220 spaced circumferentially around sidewall 208. When capsular ring 220 is implanted in the capsular bag 108 of a patient's eye 100, orifices 220 may allow aqueous humor from anterior chamber 116 to circulate within the equatorial void created by capsular ring 200 (as described in further detail below).

Figure 3A:
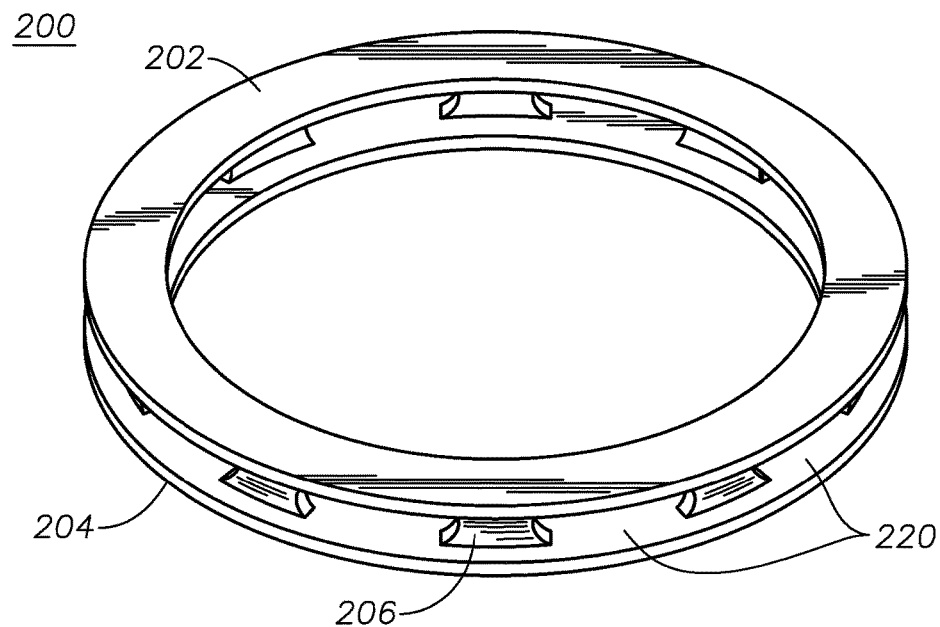
FIGS. 3A-3B illustrate an alternative configuration of the asymmetric capsular ring, according to certain embodiments of the present disclosure.
Figure 3B:
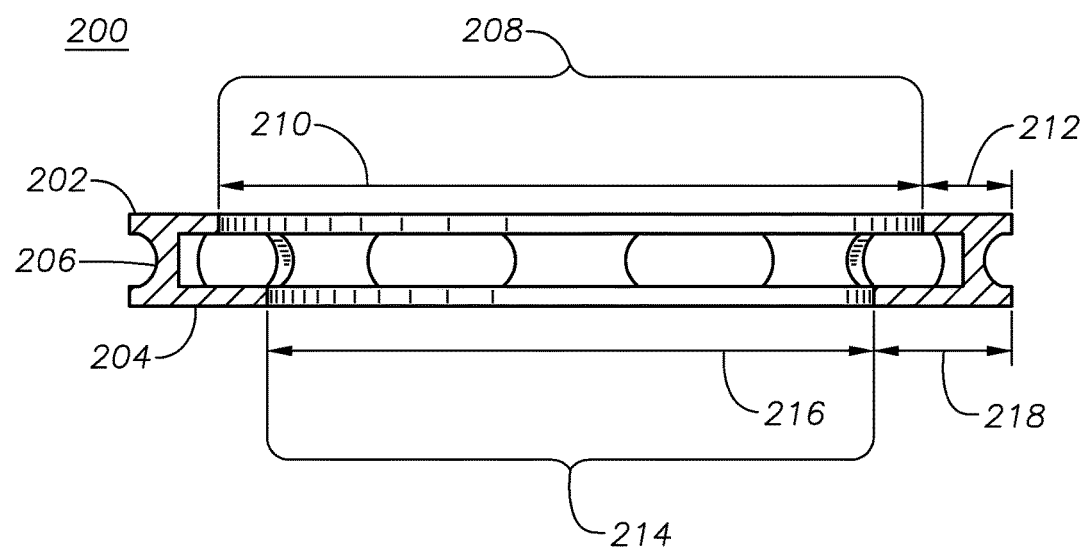

In certain embodiments, sidewall 206 may define a generally flat outer profile (as illustrated in FIGS. 2A-2B). In alternative embodiments, sidewall 206 may define a generally concave outer profile. For example, FIGS. 3A-3B illustrate an alternative configuration of asymmetric capsular ring 200 in which sidewall 206 defines a generally concave outer profile. Although sidewall 206 is depicted and described as particular outer profile shapes for exemplary purposes, the present disclosure contemplates that sidewall 206 may define any suitable outer profile shape, according to particular needs.

Although anterior ring 202, posterior ring 206, and sidewall 206 are described above as distinct components coupled together for simplicity, the present disclosure contemplates that anterior ring 202, posterior ring 206, and sidewall 206 may each be regions of a single unitary structure. In other words, the present disclosure contemplates that anterior ring 202, posterior ring 206, and sidewall 206 may each be separately formed components that are fused together in any suitable manner or that capsular ring may be formed as a unitary component with anterior ring 202, posterior ring 206, and sidewall 206 referencing different portions of that unitary component.

Capsular ring 200 may be constructed from a structurally deformable biocompatible material or combination of such materials, enabling capsular ring 200 to elastically or plastically deform without compromising its integrity. For example, capsular ring 200 may be made from a self-expanding biocompatible material, such as Nitinol. As another example, capsular ring 200 may be made from a resilient polymer, such as silicone or 2-phenyl ethyl acrylate and 2-pheylethyl methacrylate known under the name AcrySof®. As yet another example, capsular ring 200 may be made from an elastically compressed spring temper biocompatible material. Other materials having shape memory characteristics may also be used. In certain embodiments, the material composition of capsular ring 200 resiliently biases the ring toward the expanded condition.

Figure 4:
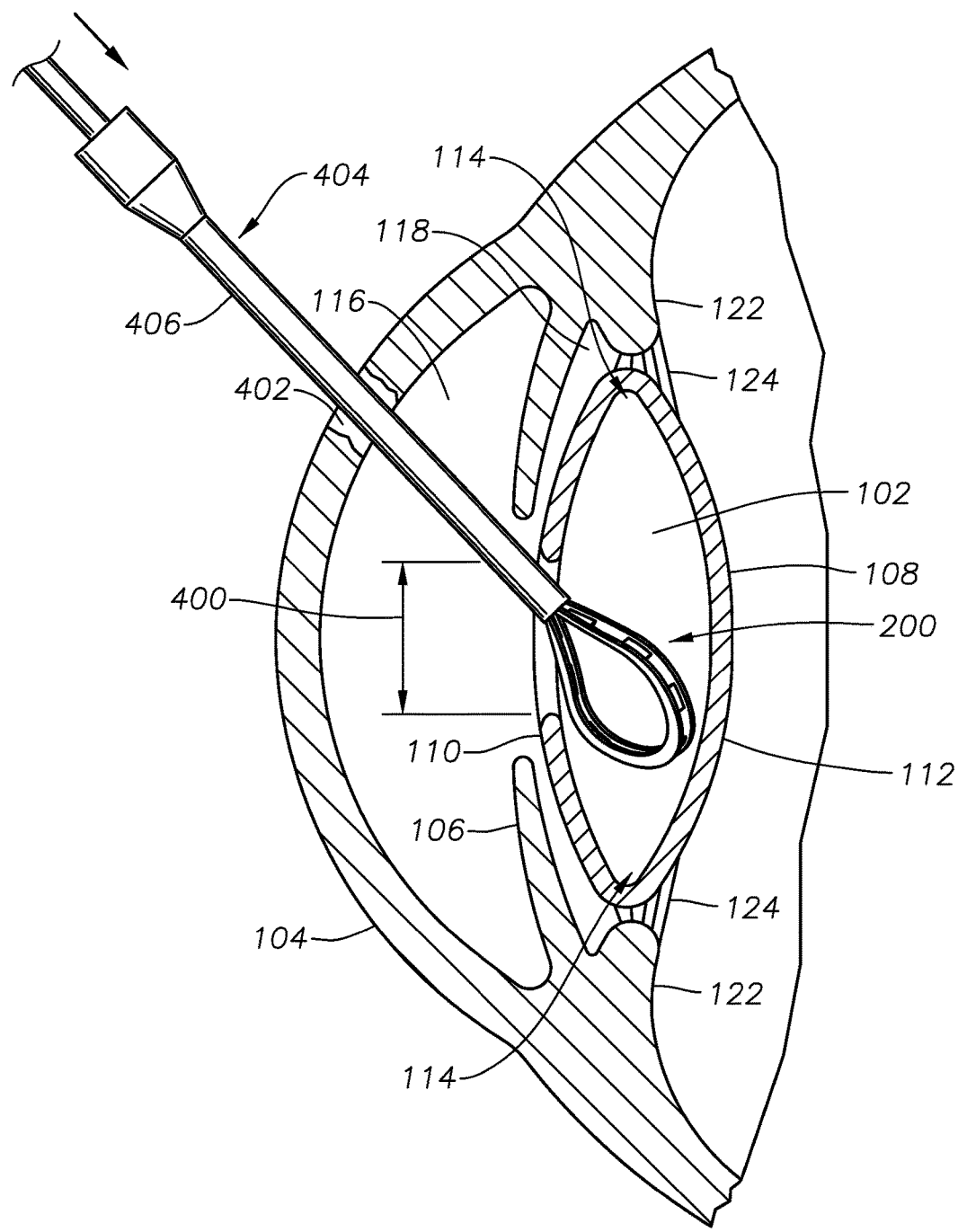
FIG. 4 illustrates an example mechanism for inserting either the capsular ring depicted in FIGS. 2A-2B or the capsular ring depicted in FIGS. 3A-3B into the capsular bag of a patient's eye, according to certain embodiments of the present disclosure.

The above-discussed structurally deformable materials may allow capsular ring 200 to be restrained in a low profile configuration during delivery into the eye and to resume and maintain its expanded shape in vivo after the delivery process. For example, FIG. 4 illustrates an example mechanism for inserting capsular ring 200 into the capsular bag 108 of a patient's eye 100, according to certain embodiments of the present disclosure. The capsular bag 108 of eye 100 is shown with an anterior capsulorhexis 400 (i.e., an area of the anterior capsule 110 that has been removed) and with the natural lens removed. As a result, an incision 402 in the cornea 104 may allow for the insertion of capsular ring 200 into capsular bag 108 via incision 402 and anterior capsulorhexis 400.

In certain embodiments, capsular ring 200 may be inserted into the capsular bag 108 of a patient's eye 100 using a delivery instrument 404. A lumen 406 of delivery instrument 404 may be inserted through corneal incision 402 (e.g., a 1.8-4 mm incision), through anterior capsulorhexis 400, and into the capsular bag 108. Capsular ring 200 may be housed in the lumen 406 in a compressed (i.e., unexpanded) state. Delivery instrument 404 may include a plunger 408 configured to translate longitudinally within lumen 406 such that plunger 408 may push capsular ring 200 out of the distal end of lumen 406 and into capsular bag 108. Upon exiting the distal end of lumen 406 of delivery instrument 404, capsular ring 200 may assume the expanded position and may be located along the equatorial region 114 of capsular bag 108.

Although a particular technique for inserting capsular ring 200 into the capsular bag 108 of a patient's eye 100 has been described, the present disclosure contemplates that capsular ring 200 may be inserted into the capsular bag 108 of a patient's eye 100 using any suitable technique, according to particular needs.

Figure 5:
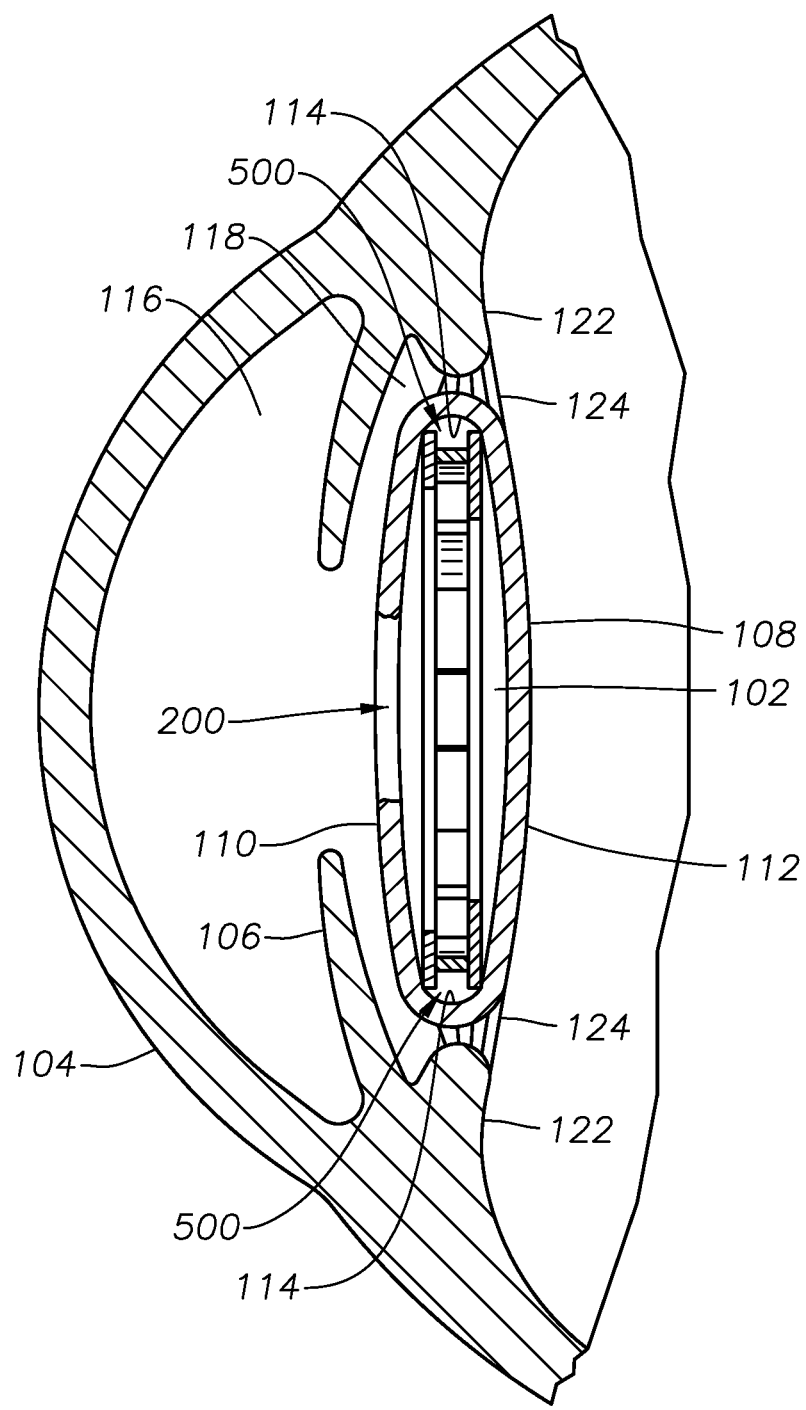
FIG. 5 illustrates a cross-section of the capsular ring depicted in FIGS. 2A-2B after insertion into the capsular bag of a patient's eye, according to certain embodiments of the present disclosure.

FIG. 5 illustrates a cross-section of capsular ring 200 after insertion into the capsular bag 108 of a patient's eye 100, according to certain embodiments of the present disclosure. When positioned along the equatorial region 114 of capsular bag 108, capsular ring 200 may maintain separation between anterior capsule 110 and posterior capsule 112. In other words, capsular ring 200 may keep capsular bag 108 open. As a result, aqueous humor located in the anterior chamber 116 may be allowed to circulate through capsular bag 108 by passing through anterior capsulorhexis 400. This circulation may help to prevent migration of lens epithelial cells.

In addition to keeping capsular bag 108 open, capsular ring 200 may create an equatorial void 500 when seated along the equatorial region 114 of the capsular bag 108. Additionally, equatorial void 500 may be bounded by the sharp corners of anterior ring 202 and posterior ring 204 engaging the capsular bag 108, and these sharp edges may help prevent the migration of lens epithelial cells from the equatorial region 114 to other areas of the capsular bag 108. In other words, the equatorial void 500 may serve to contain lens epithelial cells.

Additionally, orifices 220 is sidewall 206 may allow the aqueous humor circulating through capsular bag 108 to also circulate within equatorial void 500, further helping to prevent migration of lens epithelial cells. The above discussed ways in which capsular ring 200 helps to prevent migration of lens epithelial cells may collectively reduce the likelihood of PCO.

Figure 6:
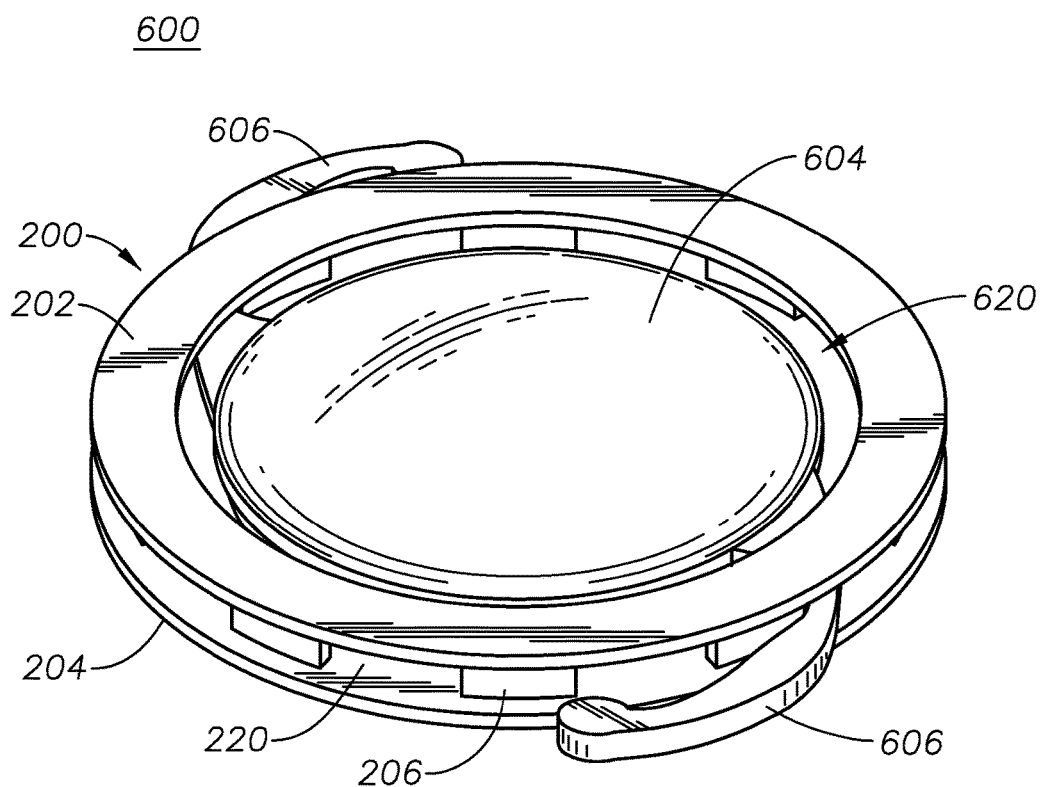
FIG. 6 illustrates an example IOL system including the capsular ring depicted in FIGS. 2A-2B, according to certain embodiments of the present disclosure.

FIG. 6 illustrates an example IOL system 600 including capsular ring 200, according to certain embodiments of the present disclosure. In addition to the capsular ring 200, IOL system 600 may include a lens 602 configured to interface with capsular ring 200. For example, lens 602 may include an optic 604 (e.g., any suitable optic for correcting a patient's vision) and one or more haptics 606. In certain embodiments, lens 602 may be engaged with capsular ring 200 by inserting haptics 606 through corresponding orifices 220 in the sidewall 206 of capsular ring 200. For example, a surgeon may first insert capsular ring 200 into the capsular bag 108 of a patient's eye 100 (as described above). Once the capsular ring 200 is seated in the equatorial region 114, the surgeon may then insert the lens 602 into the capsular bag 108 and feed the haptics 606 through corresponding orifices 220 in the sidewall 206 of capsular ring 200 (such that haptics 606 extend into the equatorial void 500 and engage the equatorial region 114 of capsular bag 108). As a result, lens 602 may be seated in capsular bag 108 within capsular ring 200 such that optic 604 extends across a visual axis of the patient's eye 100.

Because the posterior ring 204 of capsular ring 200 may have a greater width than anterior ring 202 (as described above), it may be less likely that, upon insertion of lens 602, a haptic 606 will be inadvertently extended through opening 214 and into the region of capsular bag 108 posterior to capsular ring 200. As a result, capsular ring 200 may facilitate safer insertion of lens 602.

Although lens 602 is depicted and described as having haptics 606 that extend through corresponding orifices 220 of capsular ring 200, the present disclosure contemplates that IOL system 600 may include a lens 602 having any suitable haptics 606 facilitating interfacing between the lens 602 and the capsular ring 200. As just one example, the present disclosure contemplates that lens 602 may have one or more haptics 606 shaped to sit between anterior ring 202 and a posterior ring 204 without extending through orifices 220 when lens 602 is engaged with capsular ring 200.

It will be appreciated that various of the above-disclosed and other features and functions, or alternatives thereof, may be desirably combined into many other different systems or applications. It will also be appreciated that various presently unforeseen or unanticipated alternatives, modifications, variations or improvements therein may be subsequently made by those skilled in the art which alternatives, variations and improvements are also intended to be encompassed by the following claims.

What is claimed is:

1. A capsular ring for insertion into a capsular bag of a patient's eye, the capsular ring comprising:
    an anterior ring defining a first opening and having a first cross-sectional width;
    a posterior ring defining a second opening and having a second cross-sectional width, wherein:
    a diameter of the first opening is greater than a diameter of the second opening; and the second cross-sectional width is greater that the first cross-sectional width; and a sidewall connecting the first ring and the second ring, the sidewall comprising a plurality of orifices spaced circumferentially around the sidewall.

2. The capsular ring of claim 1, wherein at least a portion of the capsular ring is constructed from a self-expanding, biocompatible material.

3. The capsular ring of claim 1, wherein:
the anterior ring comprises a first outer diameter;
the posterior ring comprises a second outer diameter; and
the first outer diameter is the same as the second outer diameter.

4. The capsular ring of claim 3, wherein the first outer diameter and the second outer diameter correspond to a diameter of an equatorial region of the capsular bag of the patient's eye.

5. The capsular ring of claim 1, wherein the sidewall comprises a flat outer profile.

6. The capsular ring of claim 1, wherein the sidewall comprises a concave outer profile.

7. The capsular ring of claim 1, wherein the anterior ring comprises a rectangular cross section having the first cross-sectional width.

8. The capsular ring of claim 1, wherein the posterior ring comprises a rectangular cross section having the second cross-sectional width.

9. The capsular ring of claim 8, wherein the posterior ring further comprises one or more bumps on its anterior surface.

* * * * *